US007897833B2

(12) United States Patent
Hachiya et al.

(10) Patent No.: US 7,897,833 B2
(45) Date of Patent: Mar. 1, 2011

(54) ANIMAL MODEL FOR PIGMENT SPOTS

(75) Inventors: Akira Hachiya, Cincinnati, OH (US); Penkanok Sriwiriyanont, Cincinnati, OH (US)

(73) Assignee: Kao Corporation, Tokyo (JP)

( * ) Notice: Subject to any disclaimer, the term of this patent is extended or adjusted under 35 U.S.C. 154(b) by 713 days.

(21) Appl. No.: 11/785,549

(22) Filed: Apr. 18, 2007

(65) Prior Publication Data

US 2008/0263686 A1 Oct. 23, 2008

(51) Int. Cl.
*A01K 67/00* (2006.01)

(52) U.S. Cl. ................................................ 800/8; 800/9

(58) Field of Classification Search ........................ None
See application file for complete search history.

(56) References Cited

U.S. PATENT DOCUMENTS

| | | | | |
|---|---|---|---|---|
| 5,719,126 | A * | 2/1998 | Nordlund et al. | 514/12 |
| 7,285,570 | B2 * | 10/2007 | Robinson et al. | 514/423 |
| 2006/0058252 | A1 | 3/2006 | Clawson et al. | |
| 2008/0306409 | A1 | 12/2008 | Hachiya et al. | |

OTHER PUBLICATIONS

Maeda et al. J Dermatol Sci 1997;14:199-206.*
Game et al, Wien Klin Wochenschr 2001;113:832-8.*
Platt et al. Nat Biotech Mar. 2002;20(3)231-2.*
Richardson et al. J Dermol 2006;126:79-84.*
Broome Powell. M,, et al., "Hyperpigmentation and Melanocytic Hyperplasia in Transgenic Mice Expressing the Human T24 Ha-*ras* Gene Regulated by a Mouse Tyrosinase Promoter," *Molec. Carcinogenesis* 12:82-90, Wiley-Liss, Inc. (1995).
Hachiya A:, et al., "An In Vivo Mouse Model of Human Skin Substitute Containing Spontaneously Sorted Melanocytes Demonstrates Physiological Changes after UVB Irradition," *J. Invest. Dermatol.* 125:364-372, The Society for Investigative Dermatology, Inc.(2005).
Yoshida, Y., et al., "Functional analysis of keratinocyles in skin color using a human skin substitute model composed of cells derived from different skin pigmentation types," *FASEB J.* .21:2829-2839, Federation of American Societies for Experimental Biology (Sep. 2007).
Extended European Search Report for corresponding European Application No. 08007510.4, mailed Sep. 9, 2008, European Patent Office, The Hague.
Hachiya, A., et al,, "The Paracrine Role of Stem Cell Factor/ c-kit Signaling in the Activation of human Melanocytes in Ultraviolet-B-Induced Pigmentation," *J. Invest, Dermatol.* 116:578-586, Nature Publishing Group (2001).
Imokawa, G., et al., "Differential Analysis of Experimental Hypermelanosis Induced by UVB, PUVA, and Allergic Contact Dermatitis Using a Brownish Guinea Pig Model," *Arch. Dermatol. Res.* 278:352-362, Springer Verlag; (1986).
Kawaguchi, Y., et al., "Kit Melanocytes Seem to Contribute to Melanocyte Proliferation After UV Exposure as Percursor Cells," *J. Invest. Dermatol.* 116:920-925, Nature Publishing Group (2001).
Seiberg, M., "Keratinocyte-Melanocyte Interactions During Melanosome Transfer," *Pigment Cell Res.* 14:236-242, Munksgaard International Publishers (2001).
Welsh, B.M., et al., "Topical All-*trans* Retinoic Acid Augments Ultraviolet Radiation-Induced Increases in Activated Melanocyte Numbers in Mice," *J. Invest. Dermatol.* 112:271-278, Nature Publishing Group (1999).
U.S. Appl. No. 12/073,869, inventors Hachiya, A., et al., filed Mar. 11, 2008 (Not Yet Published).
Dahlen, DD et al, "Soluble Kit receptor blocks stem cell factor bioactivity in vitro," Letik Res 25(5): 413-21 (May 2001), Elsevier Science Ltd., Oxford, UK.
Hattoyi, H. et. al, "The epidermal stem cell factor is over-expressed in lentigo senilis: implication for the mechanism of hyperpigmentation," J Invest Dermatol 122(5): 1256-65 (May 2004), Blackwell Publishing Inc., MA.
Kadono, S et al., "The role of the epidermal endothelin cascade in the hyperpigmentation mechanism of lentigo senilis," J Invest Dermatol 116(4): 571-7 (Apr. 2001), Blackwell Publishing Inc., MA.
Motokawa, T et al., "Messenger RNA levels of melanogenesis-associated genes in lentigo senilis lesions," J Dermatol Sci 37(2): 120-3 (Feb. 2005), Elsevier Ireland Ltd., Shannon, Ireland.

* cited by examiner

*Primary Examiner* — Q. Janice Li
(74) *Attorney, Agent, or Firm* — Sterne, Kessler, Goldstein & Fox P.L.L.C.

(57) ABSTRACT

An animal model for pigment spots in which the formation of pigment spots in human skin is faithfully simulated is provided. An animal model for pigment spots, wherein a black person's skin is grafted onto a non-human animal, is provided.

11 Claims, 3 Drawing Sheets
(2 of 3 Drawing Sheet(s) Filed in Color)

(A)

(B)

SCF/GAPDH
0.20
0.15
0.10
0.05
0
Light
Darkly pigmented
Endothelin -1/GAPDH
0.30
0.25
0.20
0.15
0.10
0.05
0
Light
Darkly pigmented
POMC/GAPDH
0.20
0.15
0.10
0.05
0
Light
Darkly pigmented

ANIMAL MODEL FOR PIGMENT SPOTS

FIELD OF THE INVENTION

The present invention relates to an animal model for the evaluation of skin pigment spots.

BACKGROUND OF THE INVENTION

When ultraviolet radiation reaches the skin, melanocytes are activated to promote the synthesis of melanin, and this melanin has a function of defending the skin against the harmful ultraviolet radiation. However, the synthesis of melanin leads to tanning of the skin, and if the metabolism of the skin is deteriorated, there occurs deposition of pigment, and formation of pigment spots which are cosmetically troubling. Therefore, there is a demand for a model which can be used for research on the pigmentation system in the skin, or for the evaluation of a lightening agent for suppressing pigment spot formation or removing pigment spots.

As the model for the evaluation of skin pigment spots, a three-dimensionally cultured skin, a brownish guinea pig, a C57 black mouse, a hairless SKH-2 mouse, and the like have been reported (Imokawa, G., Kawai, M., Mishima, Y., and Motegi, I. (1986) Differential analysis of experimental hypermelanosis induced by UVB, PUVA, and allergic contact dermatitis using a brownish guinea pig model. Arch. Dermatol. Res. 278, 352-362.; Welsh, B. M., Mason, R. S., and Halliday, G. M. (1999) Topical all-trans retinoic acid augments ultraviolet radiation-induced increases in activated melanocyte numbers in mice. J. Invest. Dermatol. 112, 271-278.; Kawaguchi, Y., Mori, N., and Nakayama, A. (2001) Kit(+) melanocytes seem to contribute to melanocyte proliferation after UV exposure as precursor cells, J. Invest. Dermatol. 116, 920-925.; Seiberg, M. (2001) Keratinocyte-melanocyte interactions during melanosome transfer, Pigment Cell Res. 14, 236-242.).

The three-dimensionally cultured skin contains human-derived melanocytes and epidermal cells innoculated on a support corresponding to dermis, such as collagen or the like, and it is also commercially available (Seiberg, M. (2001) Keratinocyte-melanocyte interactions during melanosome transfer. Pigment Cell Res. 4, 236-242.).

However, with regard to the three-dimensionally cultured skin, it is necessary to perform research under a presumption that the cultured skin clearly differs from the actual skin, and there is a problem that the evaluation is possible only for about 2 weeks at maximum.

Furthermore, in an animal model, since the finding that when ultraviolet radiation (UVB) is irradiated to brownish guinea pigs which have melanocytes present in the epidermis like humans, pigmentation is formed (Arch Dermatol Res 278:352-362, 1986), and research using the brownish guinea pigs have been actively conducted (Hachiya, A., Kobayashi, A., Ohuchi, A., Takema, Y., and Imokawa, G. (2001) The paracrine role of stem cell factor/c-kit signaling in the activation of human melanocytes in ultraviolet-B-induced pigmentation. J. Invest. Dermatol., 116, 578-586.).

Also, for the hairless SKH-2 mouse and the like are known and used as a model for ultraviolet-induced pigmentation in addition to brownish guinea pigs (Welsh, B. M., Mason, R. S., and Halliday, G. M. (1999) Topical all-trans retinoic acid augments ultraviolet radiation-induced increases in activated melanocyte numbers in mice. J. Invest. Dermatol. 112, 271-278).

However, since the genetic information of the brownish guinea pig has not been known yet, when attempting to interpret the function of a factor, it is required to verify every time as to whether or not a gene probe or an antibody used in other species could be used, and perform the interpretation. Also, the hairless SKH-2 mouse has problems, when compared with humans, that the thickness of the epidermis is obviously different, and the like.

Because of the above reasons, the creation of a model in which the pigmentation system of the human skin, particularly formation of pigment spots, is simulated faithfully and maintained stably for a long time, is desired.

SUMMARY OF THE INVENTION

The present invention relates to the following.

(1) An animal model for evaluating pigment spots, wherein a black person's skin is grafted onto a non-human animal.

(2) A method of producing an animal model for evaluating pigment spots, which comprises grafting a black person's skin onto a non-human animal, and raising the animal for at least 6 months after the grafting.

(3) A method of evaluating or screening a pigment spot formation suppressant or a pigment spot remover, wherein the animal model of (1) is used.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
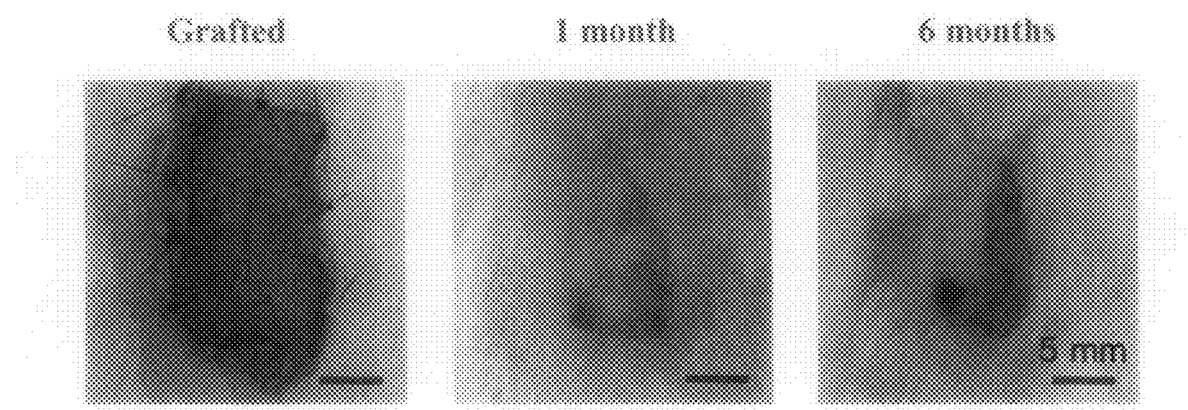
FIG. 1A is a photograph showing changes over time in the darkly pigmented area after grafting of a black person's foreskin.
FIG. 1B is a graph showing changes over time in the ratio of the darkly pigmented area relative to the entire area of the grafted black person's foreskin after grafting of the foreskin.
Figure 1:
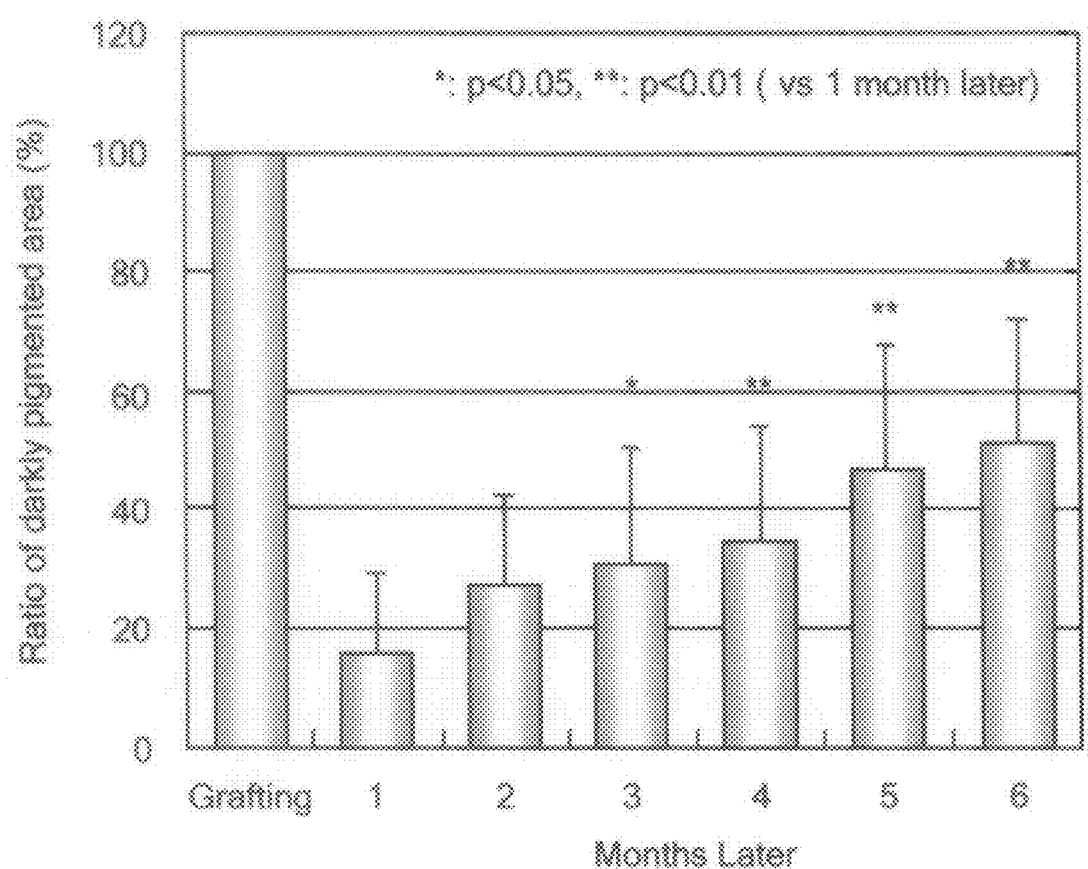

The present invention provides an animal model for evaluating pigment spots, in which pigment spot formation in human skin is faithfully simulated.

The inventors of the present invention examined various skin pigment spot models, and found that when a black person's skin is grafted to an immunodeficient mouse, pigmentation such as pigment spots is formed, and at the same time, increases in the expression of cytokines and the epidermal thickness are observed in the pigment spot area, thus the animal is able to serve as an animal model for pigment spots.

Since the animal of the present invention allows pigment spot formation to be authentically simulated and maintained stably for a long time, the animal is a potential model for evaluating pigment spots in human skin. Thus, upon using the model, evaluation or screening of a pigment spot formation suppressant or the like can be carried out.

The animal model for evaluating pigment spots of the present invention can be prepared by grafting a black person's skin onto a non-human animal.

The black person's skin that can be used for the present invention may be the skin from any of an infant, a child and an adult, as long as it is the skin derived from a black person (African descent or dark skin), and the site of use is also not limited. For example, the foreskin of an adult or an infant, or the skin extracted during surgery or pathological autopsy can be used, while it is preferable to use the foreskin from the viewpoint of procurement.

The non-human animal that can be used in the present invention is preferably, for example, mammals such as a rat, rabbit, monkey and the like, and among the mammals, rodents such as, for example, a mouse, rat, hamster and the like are preferred from the viewpoint of the convenience in skin grafting. In addition, the non-human animal is preferably an animal with suppressed immunological competence or an immunodeficient animal, and more preferably an immunodeficient animal, so as to suppress detachment of the grafted skin.

The immunodeficient mouse may be exemplified by an immunodeficient mouse such as SCID mouse, BALBcA-nu/Scid, B-17/Icr-Scid or the like, or an immunodeficient rat such as F344Jca-rnu or the like. Furthermore, in the case of raising an immunodeficient non-human animal, it is preferable to perform the raising under aseptic conditions.

The grafting of a black person's skin may be performed using known methods. For example, it may be performed according to the method described below.

A black person's skin is aseptically collected in its full-thickness or split-thickness. The collected skin can be preserved in sterilized physiological saline or in an appropriate culture medium, for example, in Dulbecco's Modified Eagle's Medium (DMEM) culture medium supplemented with L-glutamine and antibiotic/antimycotic (Invitrogen, CA), at 4 to 20° C. until it is used for grafting to an animal.

Then, the recipient animal is anesthetized with ether or the like, and then the region in which the skin is removed in a size of, for example, 2 to 3 cm in diameter is produced on the dorsal side. It is favorable to shave hair, if necessary. Thereafter, a black person's skin graft which is slightly smaller than the region is grafted onto the region on the dorsal side of the animal.

Then, by use of a conventional method, the graft is sutured with a thread of mono filament base, nylon or the like, preferably with a long-chained aliphatic nylon thread, at an interval of about 5 mm. In this case, as the graft and the region are rendered identical in shape and sutured at a uniform tension, the graft and the graft bed can adhere tightly to facilitate the engraftment of the graft.

After the grafting, a topical anesthetic of amide type or the like is administered at the boundary of the grafted skin to induce sensory denervation, and the mouse is nursed. Typically, 3 to 5 weeks are required to complete engraftment of the graft.

Thus, the grafted black person's skin graft undergoes decolorization of the black color of the skin in 7 to 15 days after the grafting, and after about 1 month, the darkly pigmented part is reduced to less than 20% of the total area (FIG. 1). Thereafter, the darkly pigmented part stably increases, and at a point in time of 2 months after the grafting, 25 to 45%; at a point in time of 3 months after the grafting, 30 to 50%; at a point in time of 4 months after the grafting, 35 to 55%; at a point in time of 5 months after the grafting, 40 to 60%; and at a point in time of 6 months after the grafting, 50% or greater on average, typically 50 to 60%, of the area becomes darkly pigmented (FIG. 1). Thereafter, the darkly pigmented part no longer increases and is maintained stably.

Figure 2:
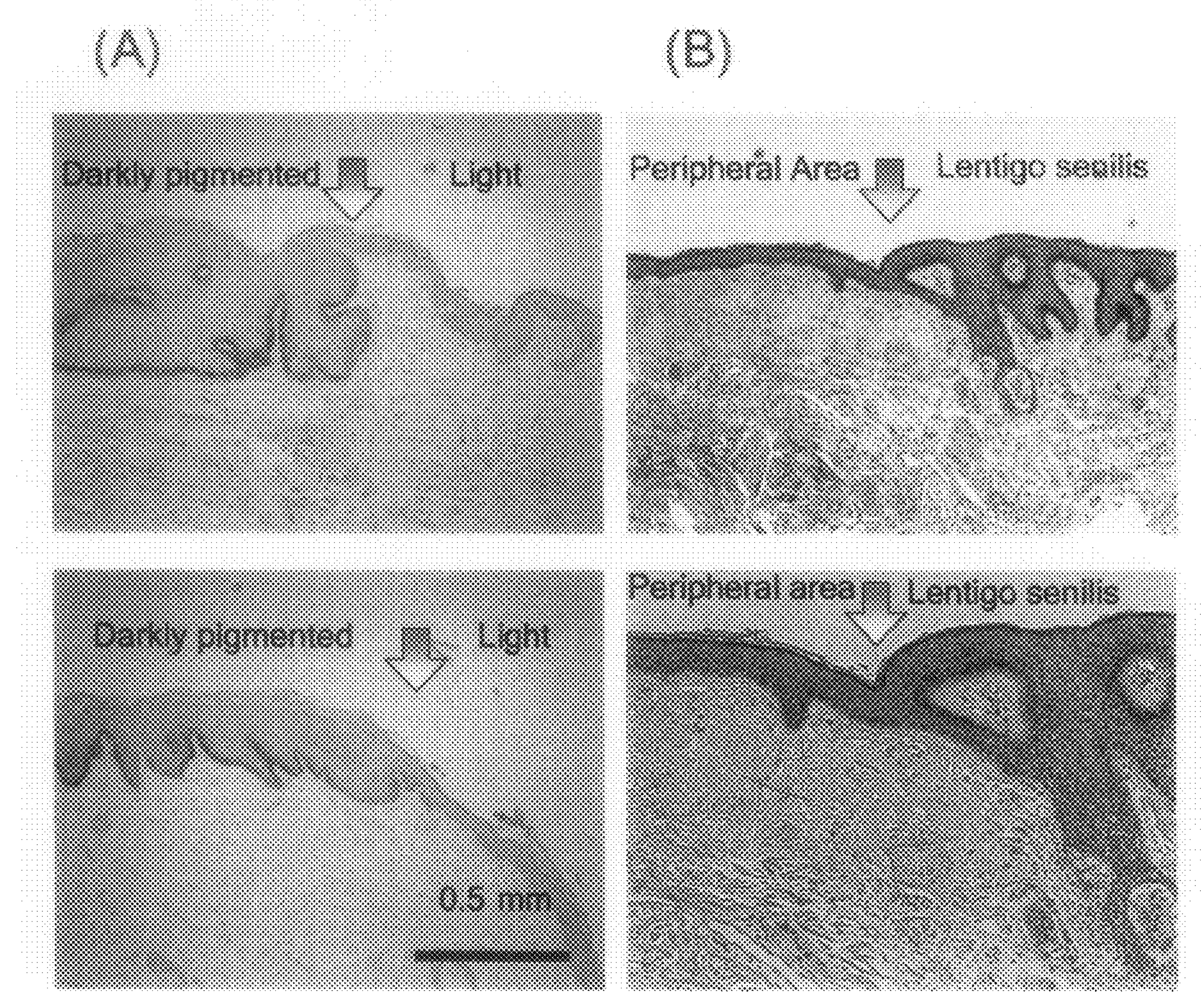
FIG. 2 is a set of photographs showing Fontana-Masson stainings of grafted foreskins and lentigo senilis. (A) Grafted foreskin. (B) Lentigo senilis.

About 7 months after the grafting, the grafted skin is collected to include darkly pigmented parts and light parts, and the collected skin is subjected to Fontana-Masson staining. As the cross-section of the skin is observed, the darkly pigmented part where melanin granules are stained exhibits a significant increase in thickness of the epidermis, as in the case of lentigo senilis (FIG. 2).

Figure 3:
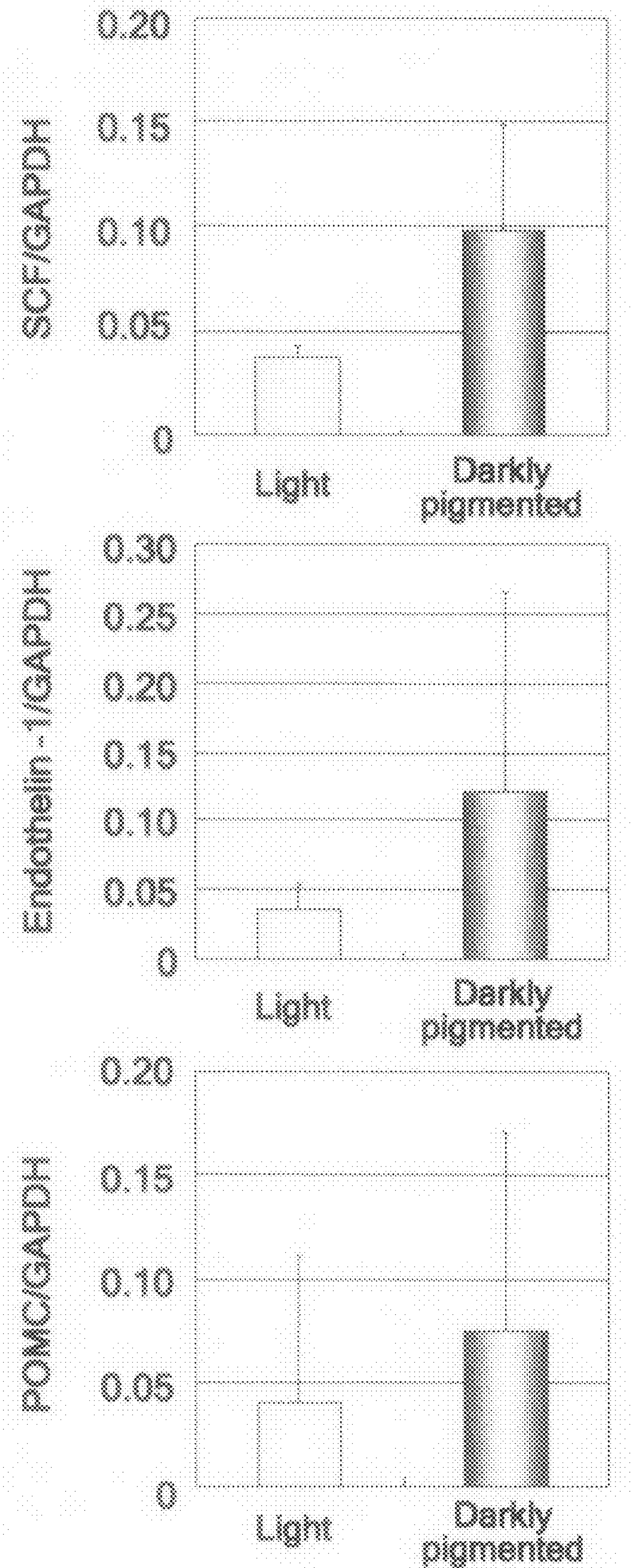
FIG. 3 is a set of graphs showing the amount of expression of genes of cytokines for melanin synthesis (amount of mRNA) in the light part and darkly pigmented part of the grafted foreskin. (A) SCF (stem cell factor). (B) Endothelin-1. (C) POMC (Precursor of $\alpha$ melanocyte stimulating hormone, Pro-opiomelanocortin).

Furthermore, in the darkly pigmented part, the expression of genes of cytokines associated with melanin synthesis (Endothelin-1 (prepro-endothelin-1), SCF, a Melanocyte Stimulating Hormone (POMC) gene) is increased (FIG. 3).

As such, the darkly pigmented part formed upon the skin grafting of the present invention shows closely similar characteristics regarding the melanin synthesis leading to the appearance of pigment spots.

Therefore, by using the animal or the grafted skin of the present invention, evaluation or screening of a medicament, cosmetic product or the like intended to suppress the formation of skin pigment spots or to remove formed pigment spots can be implemented.

For example, it is possible to implement the evaluation or screening of a pigment spot formation suppressant or a pigment spot remover, by analyzing the RNA derived from the epidermis of the darkly pigmented part (pigment spot part) and the light part (non-pigment spot part) of the grafted skin in the animal model for pigment spots of the present invention, measuring the amount of expression of genes of cytokines such as Endothelin-1, SCF, α Melanocyte Stimulating Hormone (POMC) and the like, and using the results as an index; or by measuring the skin color using a calorimeter, and using the results as an index. In addition, the term "pigment spot" as used herein includes lentigo senilis, pigmentation after inflammation, and darkening of the skin due to pigmentation such as freckles and the like.

The evaluation or screening of a pigment spot formation suppressant or a pigment spot remover can be performed by, specifically, administering an appropriate amount of test substance to the animal of the present invention via an administration route involving transdermal, injection, oral or the like, and determining the effect of the test substance.

EXAMPLES

1. Method of Preparing Grafted Skin and Changes in the Darkly Pigmented Part Over Time Foreskin derived from African descent was obtained from the University of Cincinnati Hospital and Christ Hospital, and then immediately washed with phosphate buffered saline (PBS). Then, the foreskin was trimmed to a suitable size (about 1.5 cm×1.5 cm to about 2.0 cm×2.0 cm). Until transferred to an animal facility, the foreskin was immersed in Dulbecco's Modified Eagle's Medium (DMEM) containing L-glutamine and antibiotic/antimycotic (Invitrogen, CA).

Four to six-weeks old female SCID mice (Taconic, N.Y.) were housed in an animal facility in Cincinnati Children's Hospital (Cincinnati Children's Hospital Medical Center, Cincinnati, Ohio) in a specific pathogen-free condition from the beginning to the end of the experiment.

After acclimation of about 1 week, a mouse was shaved on the dorsal side with hair clippers and a shaver, and was anesthetized in a box containing isofluorane/oxygen (3%/0.8 liter). During the grafting of foreskin, the mouse was allowed to inhale isofluorane/oxygen (2%/0.7 liter). The dorsal side skin of the mouse was excised to a size which was slightly larger than the trimmed foreskin (about 2 to 3 cm in diameter), and the mouse skin and the foreskin were sutured according to a standard method. The boundary of the grafted foreskin and the mouse skin was subjected to a sensory denervation treatment with sensorcaine. After the grafting, the mouse was maintained at 37° C. for 1 hour, or until it woke up from anesthesia.

Since the grafted foreskin completely conglutinates with the mouse skin in about 1 month after grafting, the grafted foreskin was photographed from that point in time and at an interval of 1 month using a digital camera, and a relative ratio of the area of the darkly pigmented part to the entire area was calculated.

As shown in FIG. 1, the area of the darkly pigmented part at the time point of 1 month after the grafting was less than 20% of the entire area. But, the area stably increased thereafter, and at the point in time of 6 months after the grafting, 50% or larger area on average was found to be covered by the darkly pigmented part. After then, most of the grafted foreskins were not acknowledged to have such stable increases in the area.

2. Comparison of Sections of Grafted Skin

After about 7 months of the foreskin grafting, at which time the increase in area of the darkly pigmented part became stable, the grafted foreskin was collected, and a sample section was prepared to contain darkly pigmented parts and light parts. After the preparation of the section, Fontana-Masson staining was attempted according to a standard method, so that melanin granules could be clearly detected.

The section was compared with a lentigo senilis (age spot) sample which was obtained from a contract laboratory (Stephens &Associates) in Dallas, the darkly pigmented part in the grafted foreskin was found to have significant thickening of the epidermis, as in the lentigo senilis (FIG. 2).

3. Expression of Endothelin-1, SCF and POMC

After about 7 months of the foreskin grafting, samples of 3 mm in diameter were collected from a darkly pigmented part and a light part in the grafted foreskin using a punch biopsy method. In order to prevent RNA from degradation, the samples were immediately immersed in RNAlater (Qiagen, Valencia, Calif.), and then total RNA was extracted using an RNeasymicrokit (Qiagen). cDNA was synthesized according to a standard method using oligo dT and Moloney murine leukemia virus reverse transcriptase. Subsequently, a probe which is specific to the genes of Endothelin-1 (prepro-endothelin-1), SCF and POMC (a precursor of a Melanocyte Stimulating Hormone) which are known as three major cytokines associated with melanin synthesis, and TaqMan Gene Expression Assays were purchased from Applied Biosystems (Foster City, Calif.), and real-time quantitative RT-PCR was performed using an ABI PRISM 7300 sequence detection system (Applied Biosystems). Expression of glyceraldehyde-3-phosphate dehydrogenase (GAPDH) was taken as the internal standard.

It has already been reported that the above-mentioned cytokines show increased expression in lentigo senilis parts (J Invest Dermatol 116: 578-586, 2001, J Invest Dermatol 122: 1256-1265, 2004, J Dermatol Sci 2: 120-123, 2005). Also as a result of the quantitative RT-PCR analysis, it was found that the expression of all of the above-mentioned cytokines was higher in the darkly pigmented part compared to the light part (FIG. 3). In particular, the expression of SCF was significantly ($p<0.05$) higher in the darkly pigmented part.

4. Discussion

From the above, in the darkly pigmented part of the grafted skin of the present invention, increased expression was observed for the genes of Endothelin-1 (prepro-endothelin-1), SCF and POMC, which have been actually observed to show increased expression in lentigo senilis parts. Furthermore, as it is being found that lentigo senilis parts are associated with increased expression of inflammatory cytokines such as tumor necrosis factor alpha and the like (J Invest Dermatol 116: 571-577, 2001), or with epidermal thickening, the darkly pigmented parts of the grafted skin were also observed to have definite epidermal thickening as in lentigo senilis parts.

Therefore, it is contemplated that there is a high possibility that the characteristics of the grafted skin related to melanin synthesis is closely similar to the pigment spots.

The invention claimed is:

1. An animal model for evaluating pigment spots, wherein said model is an immunodeficient mouse or an immunodeficient rat onto which a black person's skin has been grafted, wherein within a month after said grafting, the grafted skin comprises (a) darkly pigmented parts and (b) light parts from decolorization after grafting.

2. The animal model according to claim 1, wherein said animal model is an immunodeficient mouse.

3. The animal model according to claim 1, wherein the area of the darkly pigmented part comprises up to 60% of the area of the grafted skin.

4. The animal model according to claim 3, wherein the expression of a gene of at least one cytokine selected from the group consisting of Endothelin-1, SCF and POMC is increased in the darkly pigmented part as compared to the light part.

5. A method of preparing a skin graft for evaluating the formation of pigment spots in said graft, said method comprising grafting a black person's skin onto an immunodeficient mouse or an immunodeficient rat, and raising said mouse or rat after said grafting, wherein within one month after said grafting, the grafted skin comprises (a) darkly pigmented parts and (b) light parts from decolorization after grafting.

6. A method of evaluating or screening a pigment spot formation suppressant or a pigment spot remover, wherein said method comprises administering said suppressant or said remover to the immunodeficient mouse or the immunodeficient rat animal model of any one of claims 1 to 4, and evaluating the effect of said suppressant or said remover on the grafted skin.

7. The method of claim 6, wherein said method evaluates whether said suppressant suppresses the formation of darkly pigmented parts in the grafted skin.

8. The method of claim 6, wherein said method evaluates the thickness of the epidermis of darkly pigmented parts of the grafted skin.

9. The animal model of claim 2, wherein said immunodeficient mouse is a BALBcA-nu/Scid mouse or a B-17/Icr-Scid mouse.

10. The animal model of claim 1, wherein said animal model is an immunodeficient rat.

11. The animal model of claim 10, wherein said immunodeficient rat is an F344Jca-rnu rat.

* * * * *